(12) United States Patent
Jain et al.

(10) Patent No.: US 9,776,943 B2
(45) Date of Patent: Oct. 3, 2017

(54) CATALYST RECOVERY AND RECYCLING PROCESS DURING AROMATIC CARBOXYLIC ACID PRODUCTION

(71) Applicant: Reliance Industries Limited, Mumbai (IN)

(72) Inventors: Suresh Shantilal Jain, Thane (IN); Pavankumar Aduri, Thane (IN); Vivek Shankaranarayanan, Hyderabad (IN); Parasuveera Uppara, Navi Mumbai (IN)

(73) Assignee: Reliance Industries Limited, Mumbai (IN)

( * ) Notice: Subject to any disclaimer, the term of this patent is extended or adjusted under 35 U.S.C. 154(b) by 0 days.

(21) Appl. No.: 15/116,913

(22) PCT Filed: Feb. 19, 2015

(86) PCT No.: PCT/IB2015/051258
§ 371 (c)(1),
(2) Date: Aug. 5, 2016

(87) PCT Pub. No.: WO2015/125096
PCT Pub. Date: Aug. 27, 2015

(65) Prior Publication Data
US 2017/0166508 A1    Jun. 15, 2017

(30) Foreign Application Priority Data
Feb. 20, 2014    (IN) .......................................... 598/14

(51) Int. Cl.
C07C 51/48 (2006.01)
C07C 51/265 (2006.01)
B01J 23/889 (2006.01)
B01D 17/02 (2006.01)

(52) U.S. Cl.
CPC ........ C07C 51/265 (2013.01); B01D 17/0208 (2013.01); B01J 23/8892 (2013.01); C07C 51/48 (2013.01)

(58) Field of Classification Search
CPC ... C07C 51/48; C07C 51/265; B01D 17/0208; B01J 23/8892
USPC .......................................................... 502/29
See application file for complete search history.

(56) References Cited

U.S. PATENT DOCUMENTS 5,955,394 A     9/1999  Kelly
6,960,693 B2   11/2005  Xi et al.

FOREIGN PATENT DOCUMENTS

EP    0088436 A2     12/1982
WO    2010032263 A3   3/2011
WO    2013164852 A1  11/2013

OTHER PUBLICATIONS

International Search Report issued in PCT/IB2015/051258 dated Jul. 8, 2015 (2 pages).
Written Opinion of the International Searching Authority issued in PCT/IB2015/051258 dated Jul. 8, 2015 (6 pages).

*Primary Examiner* — Edward Johnson
(74) *Attorney, Agent, or Firm* — Osha Liang LLP

(57) ABSTRACT

The present disclosure provides a process for recovering and recycling a catalyst from the mother liquor generated during the production of aromatic carboxylic acids. The process comprises treating the mother liquor with an alkyl aromatic compound and further treating the first aqueous layer obtained with an ionic liquid to obtain a catalyst rich aqueous mixture. The catalyst rich aqueous mixture is recycled to the oxidation reactor.

12 Claims, 1 Drawing Sheet

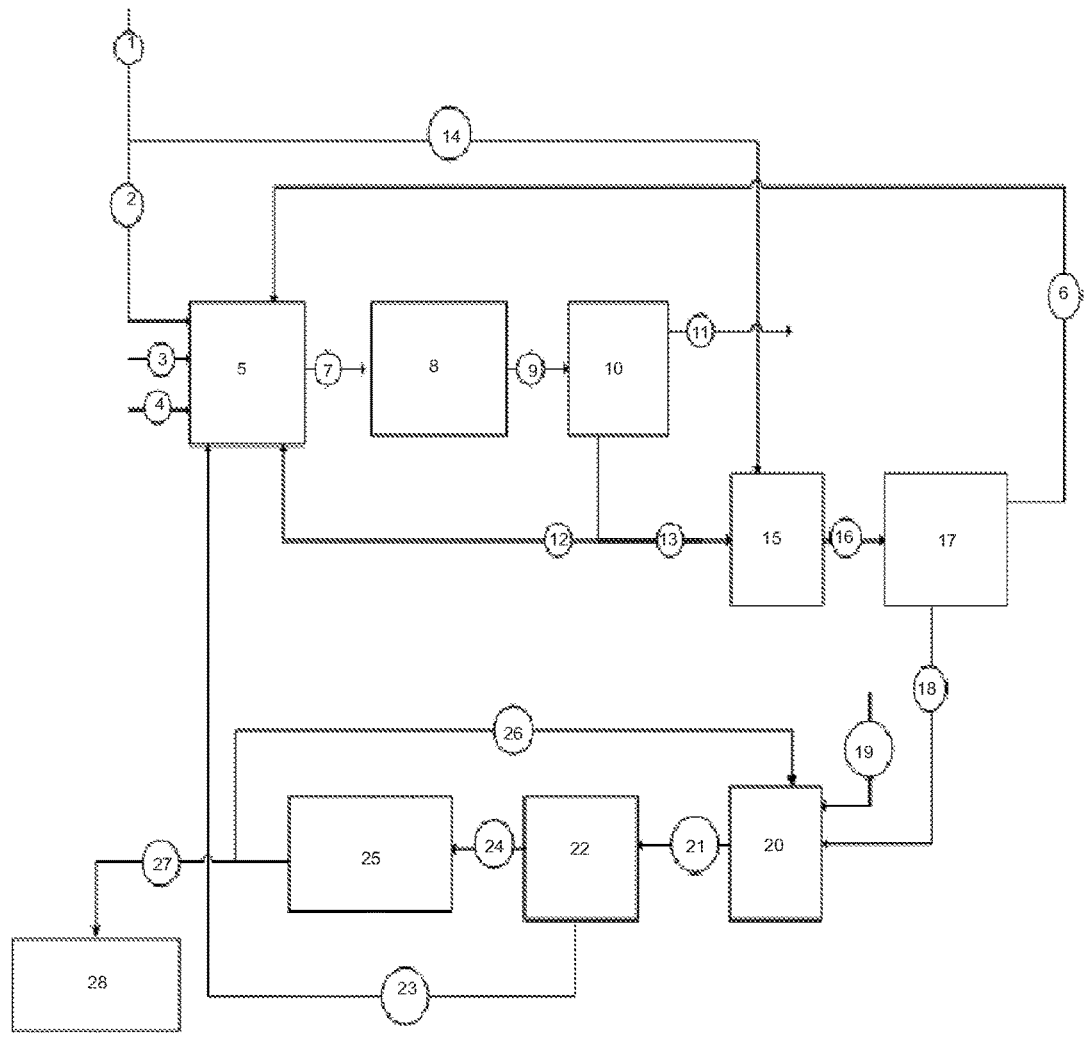

US 9,776,943 B2

CATALYST RECOVERY AND RECYCLING PROCESS DURING AROMATIC CARBOXYLIC ACID PRODUCTION

FIELD

The present disclosure relates to a process for recovering and recycling a catalyst from the mother liquor generated during aromatic carboxylic acid production.

DEFINITION

The term "catalyst" as used herein can include one catalyst or more than one catalyst or a catalyst system.

BACKGROUND

Aromatic carboxylic acid production involves catalytic oxidation of alkyl aromatics. The catalysts used in these processes are mainly transition metals or transition metal compounds. From process optimization point of view, it is crucial to have valuable chemicals and catalysts recovered and recycled without affecting the quality of the final product.

Terephthalic acid is produced by reacting p-xylene with molecular oxygen in the presence of a catalyst with acetic acid as solvent. The reaction results in formation of water and other by-products in dissolved form. Acetic acid gets diluted in water, formed as a side product and therefore, needs to be purified before it is recycled into the p-xylene oxidation section as unpurified/diluted acetic acid hampers the rate of p-xylene oxidation.

The solvent recovery area in the terephthalic acid plant consists of a plurality of high temperature flashing and evaporation units. The main function of this plurality of units is to recover the acetic acid from the mother liquor of p-xylene oxidation. The organic impurities that are formed as co and/or side-products during p-xylene oxidation, in high concentrations, impact both the quality and utilization of the plant. The solvent recovery section of the terephthalic acid plant is a highly energy intensive unit and high impurity concentration in this network causes frequent breakdowns and necessitates washing with caustic soda. Further, during solvent recovery, the mother liquor is subjected to high temperature flashing and evaporation for recovering acetic acid. The residue containing benzoic acid with other organic acid impurities, terephthalic acid and its oxidation intermediates and the catalyst, is flaked and sold off as crude benzoic acid. This result in the loss of the precious catalyst, that can be reused.

WO2010032263 suggests a process for recovering catalyst from the waste stream after flashing and evaporation of acetic acid. Initially, the reactor effluent produced during the manufacture of terephthalic acid is diluted with water in the weight ratio 1:1 to 1:12. Subsequently, the diluted effluent is chilled to a temperature ranging from 5 to 20° C. under stirring followed by separating the aqueous phase rich in the spent oxidation catalyst from the solid phase rich in organic compounds. Finally, the aqueous phase is concentrated to recover the spent oxidation catalyst and water. The process according to WO2010032263 includes a step of chilling the effluent, which adds up to the overall process costs.

In view of the above, there exists a need to have a catalyst recovery and recycle process having low energy and utility requirements.

OBJECTS

Some of the objects of the present disclosure which at least one embodiment is adapted to provide, are described herein below:

An object of the present disclosure is to provide a process for recovering a catalyst from a mother liquor.

Another object of the present disclosure is to provide a process for recovering a catalyst from a mother liquor that is economical.

Yet another object of the present disclosure is to provide a process for recovering a catalyst from a mother liquor that is simple and easy to handle.

Another object of the present disclosure is to provide a process for recovering a catalyst from a mother liquor that is environment friendly.

Other objects and advantages of the present disclosure will be more apparent from the following description which is not intended to limit the scope of the present disclosure.

SUMMARY

In accordance with the present disclosure there is provided a process for recovering and recycling a catalyst from a portion of mother liquor containing the catalyst generated during the production of aromatic carboxylic acids by the oxidation of alkyl aromatics. The process comprises the following steps: mixing the mother liquor with an alkyl aromatic compound in the temperature range from 20 to 80° C. to obtain a first mixture; allowing the first mixture to stand to obtain a first biphasic mixture having a first aqueous layer and a first organic layer; separating the first aqueous layer from the first biphasic mixture; treating the first aqueous layer with an ionic liquid in the temperature range from 20 to 60° C. under stirring to obtain a second mixture; allowing the second mixture to stand to obtain a second biphasic mixture having a second aqueous layer and a second organic layer; and separating the second aqueous layer from the second biphasic mixture to recover a catalyst rich aqueous mixture. The catalyst rich aqueous mixture is recycled to the oxidation reactor. The stirring can be carried out at a rotation speed in the range from 10 to 1000 rpm for a time period in the range from 1 to 60 minutes.

BRIEF DESCRIPTION OF THE ACCOMPANYING DRAWING

The disclosure will now be explained in relation to the non-limiting accompanying drawing, in which:

FIG. 1 is a flow diagram that depicts a plant process for recovering and recycling the catalyst from a portion of the mother liquor formed during the production of aromatic carboxylic acid.

DETAILED DESCRIPTION

Terephthalic acid is produced by oxidation of p-xylene in air in the presence of a catalyst. The catalyst includes, but is not limited to, an organic or an inorganic salt of cobalt, manganese chromium, copper, nickel, vanadium, iron, molybdenum, tin, cerium, zirconium, cesium and titanium, more particularly salts of cobalt and manganese; organic or inorganic bromide compound(s) such as hydrobromic acid as a promoter and acetic acid as a solvent at a pre-determined temperature and pressure. The catalyst used is expensive and therefore, its loss in any form results in additional costs in the process. This loss needs to be reduced.

In accordance with one aspect of the present disclosure, there is provided a process for recovering and recycling the catalyst from a portion of the mother liquor generated during the production of aromatic carboxylic acids by oxidation of alkyl aromatics.

The mother liquor is produced during the production of the aromatic carboxylic acids by oxidation of alkyl aromatics. The mother liquor comprises acetic acid, p-xylene, terephthalic acid and its oxidation intermediates, organic acid impurities, at least one catalyst, water, hydrobromic acid and the like.

The catalyst may be one or more organic or an inorganic salts of at least one transition metal selected from the group consisting of cobalt, manganese, chromium, copper, nickel, vanadium, iron, molybdenum, tin, cerium, zirconium, cesium and titanium and a combination thereof, or a catalyst system.

Further, the catalyst can be at least one selected from the group consisting of cobalt acetate, manganese acetate, cobalt bromide and manganese bromide.

In an embodiment of the present disclosure, the process comprises the following steps:

In the first step, the mother liquor is mixed with an alkyl aromatic compound in a reactor under stirring in the temperature range from 20 to 80° C. to obtain a first mixture.

The alkyl aromatic compound can be at least one selected from the group consisting of p-xylene, m-xylene, and o-xylene. Preferably, the alkyl aromatic compound is p-xylene.

In the second step, the first mixture is allowed to stand so that a first biphasic mixture having a first aqueous layer and a first organic layer is obtained.

In the third step, the first aqueous layer is separated from the first biphasic mixture.

In the fourth step the first aqueous layer is treated with an ionic liquid in the temperature range from 20 to 60° C. under stirring to obtain a second mixture.

The ionic liquid is used to remove the acetic acid and p-xylene from the first aqueous layer.

The ionic liquid can comprise at least one cation selected from quaternary ammonium, cholinium, sulfonium, phosphonium, guanidinium, imidazolium, pyridinium, pyrrolidinium, morpholinium, quinolinium, isoquinolium, pyrazolium piperidinium, pyrazolium, thiazolium, isothiazolium, azathiozolium, oxothiazolium, oxazinium, oxazolinium, oxazaborolium, dithiozolium, triazolium, selenozolium, oxahospholium, pyrrolium, borolium, furanium, thiphenium, phospholium, pentazolium, indolium, indolinium, oxazolium, isothirazolium, tetrazolium, benzofuranium, dibenzofuranium, benzothiophenium, dibenzothoiphenium, thiadiazolium, pyrimidinium, pyrazinium, pyridazinium, piperazinium, pyran, annolinium, phthalazinium, quinazolinium, quinoxalinium and combinations thereof, and at least one anion selected from the group that includes but is not limited to chlorides, bromides, fluorides, iodides, mesylates, tosylates, sulfates, alkyl sulfonates, phosphates, phosphonates, akyl phosphates, nitrates, nitrites, carbonates, acetates, bicarbonates, hydroxides, hexafluorophosphate, tetrafluoroborate, tricyanomethane, bis(trifluoromethanesulfonyl)imide, bis(pentafluoroethylsulfonyl)imide, bistriflamide, decanoate, bis 2,4,4-trimethylpentylphosphinate, 1,1,1,5,5,5-hexafluoro-2,4-pentanedionate, dicyanamide, bistriflamide, bis(flurorosulfonyl)imide and oxides.

Preferably, the ionic liquid is at least one selected from the group consisting of trihexyl tetradecyl phosphonium bromide, trihexyl tetradecyl phosphonium chloride, Trihexyl tetradecyl phosphonium chloride, Trihexyl tetradecyl phosphonium bromide, Trihexyl tetradecyl phosphonium decanoate, Trihexyl tetradecyl phosphonium bis 2,4,4-trimethylpentylphosphinate, Trihexyl tetradecyl phosphonium dicyanamide, Trihexyl tetradecyl phosphonium bistriflamide, Trihexyl tetradecyl phosphonium hexafluorophosphate, Trihexyl tetradecyl phosphonium tetrafluoroborate and Tetra n-octylphosphonium bromide.

In another embodiment of the present disclosure the ionic liquid is at least one selected from the group consisting of 1-Butyl-3-methylimidazolium hexafluorophosphate, 1-hexyl-3-methylimidazolium hexafluorophosphate, 1-methyl-3-octylimidazolium hexafluorophosphate, 1-butyl-2,3-dimethylimidazolium hexafluorophosphate, 1-butyl-3-methylimidazolium tetrafluoroborate, 1-methyl-3-octylimidazolium tetrafluoroborate, 1-butyl-3-methylimidazolium tricyanomethane, 1-butyl-3-methylimidazolium 2-(2-methoxyethoxy) ethylsulfate, 1-methyl-3-octylimidazolium 1,1,1,5,5,5-hexafluoro-2,4-pentanedionate, 1-decyl-3-methylimidazolium 1,1,1,5,5,5-hexafluoro-2,4-pentanedionate, 1-hexadecyl-3-methylimidazolium 1,1,1,5,5,5-hexafluoro-2,4-pentanedionate, 1-methyl-3-octadecylimidazolium 1,1,1,5,5,5-hexafluoro-2,4-pentanedionate, 1,2-Dimethyl-3-propylimidazolium bis(trifluoromethylsulfonyl)imide, 1-Ethyl-3-methylimidazolium bis(pentafluoroethylsulfonyl)imide, 1-Ethyl-3-methylimidazolium bis(trifluoromethylsulfonyl)imide, 1-(3-Hydroxypropyl)-3-methylimidazolium bis(trifluoromethanesulfonyl)imide, 1-Allyl-3H-imidazolium bis(trifluoromethanesulfonyl)imide, 1-butyl-2,3-dimethyllimidazolium bis(trifluoromethanesulfonyl)imide, 1-butyl-2,3-dimethyllimidazolium bis(trifluoromethanesulfonyl)imide, 1-Ethyl-3-methylimidazolium bis(flurorosulfonyl)imide 1-Ethyl-3-methylimidazolium bis(trifluoromethanesulfonyl)imide, 1-Hexyl-3-methylimidazolium bis(trifluoromethanesulfonyl)imide, 1-Hexyl-3-methylimidazolium hexafluorophosphate, 1-Octyl-3-methylimidazolium bis(trifluoromethanesulfonyl)imide, 1-propyl-2,3-dimethylimidazolium bis(trifluoromethanesulfonyl)imide.

In still another embodiment of the present disclosure, the ionic liquid is at least one selected from the group consisting of N-Tributyl-N-methylammonium dicyanamide, N-Tributyl-N-methylammonium bis(trifluoromethanesulfonyl)imide, N-Trimethyl-N-butylammonium hexafluorophosphate, N,N-Diethyl-N-methyl-N-propylammonium bis(flurorosulfonyl)imide, N,N-Diethyl-N-methyl-N-propylammonium bis(flurorosulfonyl)imide, N,N-Dimethyl-N-ethyl-N-benzyl ammonium bis(trifluoromethanesulfonyl)imide and N,N-Dimethyl-N-Ethyl-N-Phenylethylammonium bis(trifluoromethanesulfonyl)imide.

In one more embodiment of the present disclosure, the ionic liquid is at least one selected from the group consisting N-ethyl-N-methylpiperidinium bis(flurorosulfonyl)imide, N-propyl-N-methylpiperidinium bis(flurorosulfonyl)imide, N-Propyl-N-methylpiperidinium bis(trifluoromethanesulfonyl)imide, N-Propyl-N-methylpyrrolidinium bis(flurorosulfonyl)imide, N-Propyl-N-methylpyrrolidinium bis(trifluoromethanesulfonyl)imide, 1-Methyl-1-pentylpyrrolidinium bis(trifluoromethanesulfonyl)imide, N-butyl-N-methylpyrrolidinium 1,1,1,5,5,5-hexafluoro-2,4-pentanedionate, N-butyl-N-hexylpyrrolidinium 1,1,1,5,5,5-hexafluoro-2,4-pentanedionate and N-Butyl-3-methylpyridinium bis(trifluoromethylsulfonyl)imide.

In accordance with an embodiment of the present disclosure, the ratio of the amount of the first aqueous layer to the amount of the ionic liquid can be in the range from 0.5 to 5.

In the fifth step the second mixture is allowed to stand so that a second biphasic mixture having a second aqueous layer and a second organic layer is obtained.

In the sixth step, the second aqueous layer is separated from the second biphasic mixture to recover the catalyst rich aqueous mixture.

In the seventh step, the catalyst rich aqueous mixture is recycled to the oxidation reactor.

In one embodiment of the present disclosure the stirring in the first and the fourth step can be carried at a rotation speed in the range from 10 to 1000 rpm.

In another embodiment of the present disclosure the stirring in the first and the fourth step can be carried out for a time period range from 1 to 60 minutes.

In still another embodiment of the present disclosure the second aqueous solution can be directly recycled to the oxidation reactor.

In yet another embodiment of the present disclosure the second aqueous layer can be further treated to separate the dissolved organic acid impurities before recycling back to the oxidation reactor.

The accompanying drawing will now be described in detail. FIG. 1 is a flow diagram that depicts a plant process for recovering and recycling the catalyst from a portion of the mother liquor formed during the production of aromatic carboxylic acid. The apparatus for recovering and recycling the catalyst in accordance with the present disclosure comprises: a reservoir (not shown) for storing an alkyl aromatic compound such as p-xylene, a reactor 5 for carrying out the oxidation of the alkyl aromatic compound, the reactor 5 being connected to and being in fluid communication with the reservoir and receives the alkyl aromatic compound via line 2, the catalyst solution in acetic acid is fed to the reactor 5 via line 3, air is introduced into the reactor 5 as a source of oxygen through line 4. p-xylene in presence of air and the catalyst oxidizes to form a 'crude terephthalic acid' in reactor 5. The crude terephthalic acid so obtained is transferred to a crystallization chamber 8, wherein crystallization of the crude terephthalic acid takes place. A portion of the mother liquor is filtered and is transferred back to the reactor 5 via line 12. A portion of the mother liquor is purged out for further processing to maintain organic acid level in the reactor. The remaining mother liquor containing the catalyst is mixed with p-xylene coming via line 14 in a mixer 15, which can be a single or series of reactors such as continuous stirred flow reactor, static mixture, plug flow reactor and combinations thereof, followed by a decanter 17. This mixing may take place at room temperature (20° C.) or at an elevated temperature of up to 80° C. The outlet stream from mixer 15 is transferred to a decanter 17 via line 16 to separate p-xylene and an aqueous layer. In the decanter 17 a biphasic mixture is formed containing an aqueous layer and an organic layer. The aqueous layer contains the catalyst in acetic acid and the organic layer primarily contains p-xylene. Acetic acid is primarily present in the organic layer however, some residual amount of acetic acid is also present in the aqueous layer. The p-xylene stream is recycled to the oxidation reactor via line 6.

In the second stage of the process of the present disclosure the aqueous layer is removed from the decanter 17 and is transferred to a mixer 20 via line 18. The aqueous layer from the decanter 17 contains residual acetic acid, organic acids, the catalyst and p-xylene along with water. In the mixer 20 the ionic liquid is introduced via line 19. Mixer 20 can be a single or series of reactors such as a continuous stirred flow reactor, static mixture, plug flow reactor and combinations thereof followed by a decanter 22 to recover the catalyst. The ionic liquid used can be a hydrophobic ionic liquid and can be a liquid or a salt comprising an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium, piperidinium, pyrazolium, thiazolium, isothiazolium, azathiozolium, oxothiazolium, oxazinium, oxazolinium, oxazaborolium, dithiozolium, triazolium, selenozolium, oxahospholium, pyrrolium, borolium, furanium, thiphenium, phospholium, pentazolium, indolium, indolinium, oxazolium, isothirazolium, tetrazolium, benzofuranium, dibenzofuranium, benzothiophenium, dibenzothoiphenium, thiadiazolium, pyrimidinium, pyrazinium, pyridazinium, piperazinium, pyran, annolinium, phthalazinium, quinazolinium, quinoxalinium and combinations thereof, and an anion selected from the group consisting of chlorides, bromides, fluorides, iodides, mesylates, tosylates, sulfates, alkyl sulfonates, phosphates, phosphonates, akyl phosphates, nitrates, nitrites, carbonates, acetates, bicarbonates, hydroxides, hexafluorophosphate, tetrafluoroborate, tricyanomethane, bis(trifluoromethanesulfonyl)imide, bis(pentafluoroethylsulfonyl)imide, bistriflamide, decanoate, bis 2,4,4-trimethylpentylphosphinate, 1,1,1,5,5,5-hexafluoro-2,4-pentanedionate, dicyanamide, bistriflamide, bis(flurorosulfonyl)imide and oxides. The stirring is carried out for a period of 1 to 60 minutes at a rotation speed ranging from 10 to 1000 rpm. The outlet stream from the mixer 20 is transferred to the decanter 22 via line 21 to separate the ionic liquid and the aqueous stream. The aqueous stream from the decanter 22 which is rich in catalyst and acetic acid is transferred to the oxidation reactor 5 via line 23. The ionic liquid stream from the decanter 22 is transferred to an acetic acid and p-xylene recovery chamber 25 via line 24. The recycled ionic liquid stream is transferred to the mixer 20 via line 26. The ionic liquid after acetic acid and p-xylene removal is sent to the ionic liquid regeneration section 28 via line 27 for separation of organic acids and catalyst to maintain the purity level in the ionic liquid. Organic acid impurities can be separated by membrane separation. The organic acid impurities can also be converted to ester by reacting with alcohols followed by distillation for separation of ester from the ionic liquid.

The present disclosure is further described in the light of the following laboratory examples which are set forth for illustration purpose only and not to be construed for limiting the scope of the disclosure.

EXAMPLE 1

A 500 ml round bottom flask was charged with 100 g of mother liquor at 27° C. 120 g of p-xylene was mixed with the mother liquor at 27° C. to obtain the mixture. This mixture was stirred at 1000 rpm for 60 minutes using a paddle stirrer and then allowed to settle down to obtain a biphasic mixture with 64 g of aqueous layer and 156 g of organic (upper layer of p-xylene) layer. 64 g of aqueous layer was then treated with 64 g of trihexyl tetradecyl phosphonium bromide ionic liquid at 27° C. for 55 minutes and 800 rpm stirring speed using an overhead stirrer and then allowed to settle down to obtain a biphasic mixture. After layer separation, 14 g aqueous layer and 114 g of organic layer was obtained. Cobalt and manganese content in the aqueous layer was found to be 70 and 90% respectively of the initial content present in the mother liquor.

EXAMPLE 2

A 500 ml round bottom flask was charged with 100 g of mother liquor at 27° C. 120 g of p-xylene was mixed with the mother liquor at 27° C. to obtain the mixture. This mixture was stirred at 1000 rpm for 60 minutes using a paddle stirrer and then allowed to settle down to obtain a biphasic mixture with 64 g of aqueous layer and 156 g of organic (upper layer of p-xylene) layer. 50 g of aqueous layer was then treated with 50 g of trihexyl tetradecyl phosphonium chloride ionic liquid at 27° C. for 60 minutes and 800 rpm stirring speed using an overhead stirrer and then allowed to settle down to obtain a biphasic mixture. After layer separation, 3.5 g aqueous layer and 96.5 g of organic layer was obtained. Cobalt and manganese content in the aqueous layer was found to be 30 and 60% respectively of the initial content present in the mother liquor.

A typical example of the carrying out of the process in a plant is provided below in example 3.

EXAMPLE 3

1070 liters/hour of the mother liquor and 1600 liters/hour of p-xylene were sent to mixer 15. The mother liquor and p-xylene were mixed together at a temperature of 27° C. and a stirring speed of 60 rpm to obtain 2670 liters of first mixture. The first mixture was further sent to the decanter 17, where it was allowed to settle down to obtain 2065 liters of the first organic layer and 605 liters of the first aqueous layer. The first aqueous layer was separated from the first organic layer and sent to the mixer 20, where it was mixed with 670 liters of trihexyl tetradecyl phosponium bromide to obtain a second mixture. The second mixture was allowed to be stirred at a temperature of 27° C. and stirring speed of 60 rpm. The second mixture was then sent to the decanter 22 and was allowed to settle down to obtain 1190 liters of the second organic layer and 85 liters of the second aqueous layer. The second aqueous layer contains 75% of Cobalt and 92% of manganese metal catalysts as compared to the initial content in the mother liquor. The second aqueous layer was recycled to the oxidation reactor.

Technical Advantages and Economic Significance

The technical advancements offered by the present disclosure include the realization of:
a simple and cost-effective process for recovering a catalyst from the mother liquor;
the recovered catalyst of the present disclosure can be directly recycled to the oxidation reactor for further use; and
the expense for procuring fresh catalyst for every application is reduced.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

While certain embodiments of the inventions have been described, these embodiments have been presented by way of example only, and are not intended to limit the scope of the inventions. Variations or modifications in the process or compound or formulation or combination of this invention, within the scope of the invention, may occur to those skilled in the art upon reviewing the disclosure herein. Such variations or modifications are well within the spirit of this invention. The accompanying claims and their equivalents are intended to cover such forms or modifications as would fall within the scope and spirit of the invention.

The invention claimed is:

1. A process for recovering and recycling a catalyst from a portion of the mother liquor containing said catalyst generated during the production of aromatic carboxylic acids by the oxidation of alkyl aromatics, said process comprising the following steps:
   a. mixing said mother liquor with an alkyl aromatic compound in the temperature range from 20 to 80° C. in a reactor to obtain a first mixture;
   b. allowing said first mixture to stand to obtain a first biphasic mixture having a first aqueous layer and a first organic layer;
   c. separating said first aqueous layer from said first biphasic mixture;
   d. treating said first aqueous layer with an ionic liquid in the temperature range from 20 to 60° C. under stirring to obtain a second mixture;
   e. allowing said second mixture to stand to obtain a second biphasic mixture having a second aqueous layer and a second organic layer;
   f. separating said second aqueous layer from said second biphasic mixture to recover a catalyst rich aqueous mixture; and
   g. recycling said catalyst rich aqueous mixture to the oxidation reactor.

2. The process as claimed in claim 1, wherein said catalyst is an organic or an inorganic salt of at least one transition metal selected from the group consisting of cobalt, manganese, chromium, copper, nickel, vanadium, iron, molybdenum, tin, cerium, zirconium, cesium and titanium and a combination thereof.

3. The process as claimed in claim 1, wherein said alkyl aromatic compound is at least one selected form the group consisting of p-xylene, m-xylene, o-xylene, toluene and isopropyl benzene.

4. The process as claimed in claim 1, wherein said ionic liquid is at least one selected from the group consisting of trihexyl tetradecyl phosphonium bromide, Trihexyl tetradecyl phosphonium chloride, Trihexyl tetradecyl phosphonium bromide, Trihexyl tetradecyl phosphonium decanoate, Trihexyl tetradecyl phosphonium bis 2,4,4-trimethylpentylphosphinate, Trihexyl tetradecyl phosphonium dicyanamide, Trihexyl tetradecyl phosphonium bistriflamide, Trihexyl tetradecyl phosphonium hexafluorophosphate, Trihexyl tetradecyl phosphonium tetrafluoroborate, and Tetra n-octylphosphonium bromide.

5. The process as claimed in claim 1, wherein said ionic liquid is at least one selected from the group consisting of Butyl-3-methylimidazolium hexafluorophosphate, 1-hexyl-3-methylimidazolium hexafluorophosphate, 1-methyl-3-octylimidazolium hexafluorophosphate, 1-butyl-2,3-dimethylimidazolium hexafluorophosphate, 1-butyl-3-methylimidazolium tetrafluoroborate, 1-methyl-3-octylimidazolium tetrafluoroborate, 1-butyl-3-methylimidazolium tricyanomethane, 1-butyl-3-methylimidazolium 2-(2-methoxyethoxy) ethylsulfate, 1-methyl-3-octylimidazolium 1,1,1,5,5,5-hexafluoro-2,4-pentanedionate, 1-decyl-3-methylimidazolium 1,1,1,5,5,5-hexafluoro-2,4-pentanedionate, 1-hexadecyl-3-methylimidazolium 1,1,1,5,5,5-hexafluoro-2,4-pentanedionate, 1-methyl-3-octadecylimidazolium 1,1,1,5,5,5-hexafluoro-2,4-pentanedionate, 1,2-Dimethyl-3-propylimidazolium bis(trifluoromethylsulfonyl)imide, 1-Ethyl-3-methylimidazolium bis(pentafluoroethylsulfonyl)imide, 1-Ethyl-3-methylimidazolium bis(trifluoromethylsulfonyl)imide, 1-(3-Hydroxypropyl)-3-methylimidazolium bis(trifluoromethanesulfonyl)imide, 1-Allyl-3H-imidazolium bis(trifluoromethanesulfonyeimide, 1-butyl-2,3-dimethyl-limidazolium bis(trifluoromethanesulfonyl)imide, 1-butyl-2,3-dimethyllimidazolium bis(trifluoromethanesulfonyl)imide, 1-Ethyl-3-methylimidazolium bis(flurorosulfonyl)imide, 1-Ethyl-3-methylimidazolium bis(trifluoromethanesulfonyl)imide, 1-Hexyl-3-methylimidazolium bis(trifluoromethanesulfonyl)imide, 1-Hexyl-3-methylimidazolium hexafluorophosphate, 1-Octyl-3-methylimidazolium bis(trifluoromethanesulfonyl)imide, 1-Octyl-3-methylimidazolium bis(trifluoromethanesulfonyl)imide, 1-propyl-2,3-dimethylimidazolium bis(trifluoromethanesulfonyl)imide and 1-propyl-2,3-dimethylimidazolium bis(trifluoromethanesulfonyl)imide.

6. The process as claimed in claim 1, wherein said ionic liquid is at least one selected from the group consisting of N-Tributyl-N-methylammonium dicyanamide, N-Tributyl-N-methylammonium bis(trifluoromethanesulfonyl)imide, N-Trimethyl-N-butylammonium hexafluorophosphate, N,N-Diethyl-N-methyl-N-propylammonium bis(flurorosulfonyl)imide, N,N-Diethyl-N-methyl-N-propylammonium bis(flurorosulfonyl)imide, N,N-Dimethyl-N-ethyl-N-benzyl ammonium bis(trifluoromethanesulfonyl)imide and N,N-Dimethyl-N-Ethyl-N-Phenylethylammonium bis(trifluoromethanesulfonyl)imide.

7. The process as claimed in claim 1, wherein said ionic liquid is at least one selected from the group consisting of N-ethyl-N-methylpiperidinium bis(flurorosulfonyl)imide, N-propyl-N-methylpiperidinium bis(flurorosulfonyl)imide and N-Propyl-N-methylpiperidinium bis(trifluoromethanesulfonyl)imide.

8. The process as claimed in claim 1, wherein said ionic liquid is at least one selected from the group consisting of N-Propyl-N-methylpyrrolidinium bis(flurorosulfonyl)imide, N-Propyl-N-methylpyrrolidinium bis(trifluoromethanesulfonyl)imide, 1-Methyl-1-pentylpyrrolidinium bis(trifluoromethanesulfonyl)imide, N-butyl-N-methylpyrrolidinium 1,1,1,5,5,5-hexafluoro-2,4-pentanedionate, N-butyl-N-hexylpyrrolidinium 1,1,1,5,5,5-hexafluoro-2,4-pentanedionate and N-Butyl-3-methylpyridinium bis(trifluoromethylsulfonyl)imide.

9. The process as claimed in claim 1, wherein the ratio of the amount of the first aqueous layer to the ionic liquid is in the range from 0.5 to 5.

10. The process of claim 1, wherein said recovered catalyst rich aqueous mixture is further treated to separate organic acid before recycling to the oxidation reactor.

11. The process as claimed in claim 1, wherein the stirring in process steps (a) and (d) is carried out at a rotation speed in the range from 10 to 1000 rpm.

12. The process as claimed in claim 1, wherein the stirring in process steps (a) and (d) is carried out for a time period in the range from 1 to 60 minutes.

\* \* \* \* \*